| United States Patent [19] | [11] | 4,285,945 |
|---|---|---|
| Slichter | [45] | Aug. 25, 1981 |

[54] ANTITHROMBOTIC PHARMACEUTICAL COMPOSITIONS AND METHOD OF USE

[76] Inventor: Sherrill J. Slichter, 5201 SW. Canada Dr., Seattle, Wash. 98126

[21] Appl. No.: 76,510

[22] Filed: Sep. 17, 1979

[30] Foreign Application Priority Data

Feb. 8, 1979 [DE] Fed. Rep. of Germany ....... 2904736

[51] Int. Cl.³ ............................................ A61K 31/505
[52] U.S. Cl. .................................................... 424/251
[58] Field of Search ......................................... 424/251

[56] References Cited

U.S. PATENT DOCUMENTS 3,322,755   5/1967   Roch et al. ........................... 260/246

OTHER PUBLICATIONS

*Helv. Chim. Acta* 44, 236, (1961).
Therapiewoche 26, 8464–8489, (1976).

*Primary Examiner*—Frederick E. Waddell
*Attorney, Agent, or Firm*—Hammond & Littell, Weissenberger & Muserlian

[57] ABSTRACT

Antithrombotic pharmaceutical compositions containing, as a combination of active ingredients, 2,6-bis-(diethanolamino)-4-piperidino-pyrimido[5,4-d]pyrimidine and sulfinpyrazone, and a method of preventing or relieving thrombosis therewith.

3 Claims, No Drawings

ANTITHROMBOTIC PHARMACEUTICAL COMPOSITIONS AND METHOD OF USE

The Government has rights in this invention pursuant to a contract or grant awarded by the Department of Health, Education and Welfare.

This invention relates to novel antithrombotic pharmaceutical compositions containing, as a combination of active ingredients, 2,6-bis-(diethanolamino)-4-piperidino-pyrimido [5,4-d] pyrimidine and sulfinpyrazone, as well as to a method of preventing or relieving thrombosis therewith.

BACKGROUND OF THE INVENTION 2,6-Bis-(diethanolamino)-4-piperidino-pyrimido-[5,4-d] pyrimidine is disclosed in U.S. Pat. No. 3,322,755 to possess cardiovascular, spasmolytic, diuretic and CNS-stimulating properties. 1,2-Diphenyl-3,5-dioxo-4-(2-phenylsulfinyl-ethyl)-pyrazolidine (generic name: Sulfinpyrazone) is disclosed in Helv. Chim. Acta 44, 236 (1961) and has for a long time been used as an anti-gout agent. Both of these compounds were subsequently also found to have good antithrombotic properties [see Therapiewoche 26, 8464–8489 (1976)].

Both of these compounds individually, however, require relatively high dosages for achievement of an antithrombotic effect, where certain side-effects become noticeable; in the case of sulfinpyrazone these side-effects are stomach pains due to the ulcerogenic activity of this compound at high dosages.

THE INVENTION

I have discovered that when 2,6-bis-(diethanolamino)-4-piperidino-pyrimido[5,4-d]-pyrimidine and sulfinpyrazone are administered together to a warm-blooded animal, a strong synergistic antithrombotic effect is produced, whereby the individual dosages of the two compounds required for achievement of the same antithrombotic effect produced by each of them alone can be substantially reduced. This synergistic effect was ascertained in the following test model:

Warm-blooded animals which are afflicted with virulent tumors have an increased metabolism of coagulation factors and of thrombocytes. The thrombocyte metabolism can easily be measured by means of radioactively labeled thrombocytes. For this purpose blood is taken from the test animals, the erythrocytes are separated, and a suitable amount of chromium-51 is added to the platelet-rich plasma, most of which congregates in the thrombocytes. The excess chromium-51, which is in the plasma, is centrifuged off and discarded. The thrombocyte concentrate with the labeled cells is now injected i.v. into the test animals. At certain time intervals blood samples are taken and their radioactivity content is determined. The decrease in activity in the course of time, advantageously over a period of five days, is used for evaluation of the thrombocyte life time.

The normal thrombocyte life time in healthy warm-blooded animals, for instance in dogs, is about 5 days. It is shortened by various diseases; by virulent tumors, for example, to about 2 days.

After administration of the drug combination of the present invention, that is 2,6-bis-(diethanolamono)-4-piperidino-pyrimido [5,4-d]pyrimidine/1,2-diphenyl-3,5-dioxo-4-(2-phenyl-sulfinyl-ethyl)pyrazolidine in the ratio 1:1 to 1:2, to tumor-afflicted dogs at a dose of 50 to 100 mgm/kg, a nearly normal thrombocyte life time of 4.5 to 4.8 days was found.

The normalization of the thrombocyte life time is therapeutically of very great importance because the shortening of the thrombocyte life time which occurs in humans is an indication of a tendency toward thromboses. Therefore, the novel drug combination is well suited for the prevention and cure of thromboembolic diseases.

A single dose for adults contains between 25 mgm (about 0.3 mgm/kg) and 200 mgm (about 2.67 mgm/kg) of the two active substances, preferably 25 to 100 mgm 2,6-bis-(diethanolamine)-4-piperidino-pyrimido[5,4-d]-pyrimidine and 50 to 175 mgm sulfinpyrazone; the single dose is preferably administered 2 to 4 times daily.

The novel drug combination exhibits very good compatibility. Thus, for example, in the mouse at a dose of 100 mgm/kg p.o. of the combination of the present invention in the ratio of 1:1 to 1:2 of the two active substances, no toxic side-effects were noted. The $LD_{50}$ in the mouse for 2,6-bis-(diethanolamino)-4-piperidino-pyrimido [5,4-d] pyrimidine is 465 mgm/kg p.o. and 148 mgm/kg i.v., and for 1,2-diphenyl-3,5-dioxo-4-(2-phenylsulfinylethyl)-pyrazolidine it is 298 mgm/kg p.o. and 240 mgm/kg i.v.

A further object of the invention is a process for the manufacture of the drug combination according to the invention, which comprises combining 2,6-bis(diethanolamino)-4-piperidino-pyrimido [5,4-d] pyrimidine and 2,6-diphenyl-3,5-dioxo-4-(2-phenylsulfinyl-ethyl)-pyrazolidine in a weight ratio of from 10:1 to 1:10, preferably 1:1, and formulating the combination, optionally with other active substances, with inert pharmaceutical carriers and/or excipients conventional in the preparation of drugs into conventional pharmaceutical dosage unit compositions, such as tablets, coated pills, powders, capsules and the like. The combination according to the invention is preferably administered perorally.

The manufacture of tablets, coated pills, capsules, etc. is effected in known manner; for example, the tablets are prepared by direct compression of a mixture of the active ingredients and the excipients and are optionally subsequently coated with a thin shell which is compatible with the stomach and the intestine; in the manufacture of the capsules, first the powder mixture and the core with the coating are separately prepared and then filled in a commercial capsule filling machine.

The following examples illustrate a few antithrombotic pharmaceutical dosage unit compositions comprising the combination of active ingredients of the present invention and represent the best modes contemplated of using the invention. The parts are parts by weight unless otherwise specified.

EXAMPLE 1

Coated pills

The pill core composition is compounded from the following ingredients:

2,6-Bis-(diethanolamino)-4-piperidino-pyrimido [5,4-d]

| | |
|---|---|
| pyrimidine | 50.0 parts |
| Sulfinpyrazone | 50.0 parts |
| Lactose | 187.0 parts |
| Corn Starch | 105.0 parts |
| Gelatin | 6.0 parts |
| Magnesium stearate | 2.0 parts |

| -continued | |
|---|---|
| | Total 400.0 parts |

Preparation:

The active ingredients are admixed with the lactose and the corn starch, and the mixture is uniformly moistened with an aqueous solution of the gelatin. The moist mass is granulated by passing it through a 2 mm mesh screen, the granulate is dried, and the dry granulate is again passed through the screen and then admixed with the magnesium stearate. The composition is compressed into 400 mgm pill cores which are subsequently coated in conventional manner with a thin shell consisting essentially of a mixture of sugar and talcum. Each coated pill is an oral dosage unit composition containing 50 mgm of 2,6-bis-(diethanolamino)-4-piperidino-pyrimido[5,4-d] pyrimidine and 50 mgm sulfinpyrazone.

EXAMPLE 2

Hard gelatin capsules

The capsule filler composition, consisting of a powder and a coated pellet, is compounded from the following ingredients:

| (a) Powder | |
|---|---|
| Sulfinpyrazone | 50.0 parts |
| Corn starch | 158.0 parts |
| Lactose, powdered | 90.0 parts |
| Magnesium stearate | 2.0 parts |
| | Total 300.0 parts |

Preparation:

The ingredients are admixed, and the mixture is milled into a homogeneous powder.

| (b) Coated pellet | |
|---|---|
| 2,6-Bis-(diethanolamino)-4-piperidino-pyrimido [5,4-d] pyrimidine | 50.0 parts |
| Polyvinylpyrrolidone | 2.5 parts |
| Formaldehyde gelatin | 6.5 parts |
| Magnesium stearate | 1.0 parts |

| -continued | |
|---|---|
| (b) Coated pellet | |
| Lactose | 25.0 parts |
| | Total 85.0 parts |

Preparation:

The ingredients are compounded in the same way as in Example 1, and the composition is compressed into 85 mgm pellets which are subsequently coated with a shell consisting essentially of a mixture of talcum, sugar and gum arabic.

300 mgm-portions of the powder together with one coated pellet are filled into size 0 hard gelatin capsules. Each capsule is an oral dosage unit composition containing 50 mgm of 2,6-bis-(diethanolamino)-4-piperidino-pyrimido [5,4-d] pyrimidine and 50 mgm of sulfinpyrazone.

The amounts and ratios of active ingredients in these illustrative examples may be varied to achieve the dosage ranges set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. An antithrombotic pharmaceutical composition consisting essentially of an inert pharmaceutical carrier and an antithrombotic effective amount of a mixture of 2,6-bis-(diethanolamino)-4-piperidino-pyrimido [5,4-d] pyrimidine and sulfinpyrazone wherein the weight ratio of 2,6-bis-(diethanolamino)-4-piperidino-pyrimido [5,4-d] pyrimidine and sulfinpyrazone is 1:2.

2. The composition of claim 1 in unit dosage form.

3. The method of preventing or relieving thrombosis in a warm-blooded animal, which comprises perorally administering to said animal an antithrombotic effective amount of a mixture of 2,6-bis-(diethanolamino)-4-piperidino-pyrimido [5,4-d] pyrimidine and sulfinpyrazone, wherein the weight ratio of 2,6-bis(diethanolamino)-4-piperidino-pyrimido [5,4-d] pyrimidine and sulfinpyrazone in said mixture is from 1:2.

* * * * *

UNITED STATES PATENT AND TRADEMARK OFFICE
CERTIFICATE OF CORRECTION

PATENT NO. : 4,285,945
DATED : August 25, 1981
INVENTOR(S) : SHERRILL J. SLICHTER It is certified that error appears in the above—identified patent and that said Letters Patent is hereby corrected as shown below:

Preamble page, [57], line 2 of Abstract; Column 1, line 34;

and Column 4, line 45: "die-" should read -- di- --.

Preamble page, [57], line 3 of Abstract; Column 1, line 35;

and Column 4, line 46: "thanolamino" should read

-- ethanolamino --.

Column 2, lines 60 and 61: Delete "2,6-Bis-(diethanolamino)-

4-piperidino-pyrimido[5,4-d]".

Column 2, line 64: "pyrimidine    50.0 parts" should read

-- 2,6-Bis—(diethanolamino)-4-piperidino-pyrimido-

[5,4-d]pyrimidine    50.0 parts --

Signed and Sealed this

Third Day of November 1981

[SEAL]

*Attest:*

GERALD J. MOSSINGHOFF

*Attesting Officer*    *Commissioner of Patents and Trademarks*